(12) United States Patent
Dykstra et al.

(10) Patent No.: US 7,071,151 B2
(45) Date of Patent: Jul. 4, 2006

(54) COMPOSITIONS COMPRISING PHOTO-LABILE PERFUME DELIVERY

(75) Inventors: Robert Richard Dykstra, Cleves, OH (US); Lon Montgomery Gray, Florence, KY (US)

(73) Assignee: Procter & Gamble Company, Cincinnati, OH (US)

( * ) Notice: Subject to any disclaimer, the term of this patent is extended or adjusted under 35 U.S.C. 154(b) by 1 day.

(21) Appl. No.: 11/143,067

(22) Filed: Jun. 2, 2005

(65) Prior Publication Data

US 2005/0227879 A1     Oct. 13, 2005

Related U.S. Application Data

(63) Continuation of application No. 10/919,148, filed on Aug. 16, 2004, now abandoned, which is a continuation of application No. 10/217,278, filed on Aug. 12, 2002, now abandoned.

(60) Provisional application No. 60/318,662, filed on Sep. 11, 2001.

(51) Int. Cl.
*C11D 3/50* (2006.01)
(52) U.S. Cl. .......................... 510/107; 512/21; 560/104
(58) Field of Classification Search ................ 510/101, 510/102, 107; 512/2, 21; 560/104
See application file for complete search history.

(56) References Cited

U.S. PATENT DOCUMENTS 5,559,088 A    9/1996 Severns et al.

6,096,918 A    8/2000 Anderson et al.

FOREIGN PATENT DOCUMENTS

| EP | 0 936 211 A2 | 8/1999 |
|---|---|---|
| EP | 0 952 142 A1 | 10/1999 |
| JP | 05 105621 | 4/1993 |
| JP | 05 105643 | 4/1993 |

*Primary Examiner*—John R. Hardee
(74) *Attorney, Agent, or Firm*—James F. McBride; Kim W. Zerby; Steve W. Miller

(57) ABSTRACT

The present invention relates to photo-labile pro-fragrances, as well as a fragrance raw material delivery system comprising:

i) from about 0.001% to about 100% by weight, of a photo-labile pro-fragrance compound having the formula:

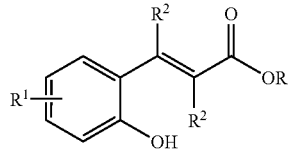

wherein OR is a unit derived from a fragrance raw material alcohol, HOR; $R^1$ is one or more electron donating groups; each $R^2$ is independently hydrogen, $C_1$–$C_{12}$ alkyl, and mixtures thereof; and ii) optionally from about 0.001% to about 50% by weight, of one or more fragrance raw materials.

2 Claims, No Drawings

COMPOSITIONS COMPRISING PHOTO-LABILE PERFUME DELIVERY

CROSS REFERENCE TO RELATED APPLICATIONS

This application claims priority under Title 35, United States Code 119(e) from application Ser. No. 10/919,148 filed Aug. 16, 2004 now abandoned which is a Continuation of application Ser. No. 10/217,278, filed Aug. 12, 2002, now abandoned which claims priority from Provisional Application Ser. No. 60/318,662, filed Sep. 11, 2001.

FIELD OF THE INVENTION

The present invention relates to compositions, inter alia, personal care lotions, laundry detergent compositions, which comprise a photo-labile perfume delivery system capable of releasing fragrance raw material alcohols. The compositions of the present invention can also comprise initial amounts of the releasable fragrance raw material alcohols thereby providing a sustained initial fragrance.

BACKGROUND OF THE INVENTION

Pro-fragrances and pro-accords have been used to enhance the delivery of fragrance raw materials and to sustain their duration. Typically pro-fragrances and pro-accords deliver alcohol, ketone, aldehyde, and ester fragrance raw materials via substrates which are triggered by one or more release mechanisms, inter alia, the acidic pH of skin, nascent moisture, shift of position of equilibrium.

Fragrances or odors not only provide a pleasant aesthetic benefit, but also serve as a signal. For example, foods, which have soured or are no longer edible, may develop smells, which are repulsive and send a signal that they are no longer palatable. Therefore, the delivery of an aroma sensory signal is also a benefit, which a pro-fragrance can provide.

However, pro-fragrances and pro-accords typically rely on the break down of a chemical species not based on accidental circumstance but on deliberate execution. There are examples of fragrance or odor releasing compounds which involve release of fragrances which are initiated by exposure to electromagnetic radiation, inter alia, UV light, however, these compounds do not have a means for controlling the release rate of the fragrances such that the formulator can ensure the fragrances will be release during a period of time which is of benefit to the consumer. The present invention provides a means for delivering fragrance raw material alcohols wherein the delivery of said alcohols is instigated by exposure to light in a manner which allows the formulator to control the rate of alcohol delivery, and control the impact of the photo-fragment by-products.

SUMMARY OF THE INVENTION

The present invention meets the aforementioned needs in that it has been surprisingly discovered that photo labile compounds can be designed to release fragrance raw materials during a period of time which is useful to the formulator of perfume comprising compositions. One drawback to compounds which release perfumes, photo-labile and otherwise, is the inability to control the release half lives of said compounds. For example, a photo labile pro-fragrance may be capable of releasing a fragrance raw material alcohol, but the release rate is such that the amount of alcohol which is released per unit time is so low that applying a sufficient amount of pro-fragrance necessary to meet aesthetic needs becomes cost prohibitive, or is limited by formulation parameters.

It has now been surprisingly discovered that aryl acrylate photo-labile compounds can be modified in a manner which allows for their utility in fragrance delivery systems. These fragrance delivery systems are useful in a wide array of compositions which deliver, in addition to other benefits, an aesthetic benefit.

The first aspect of the present invention relates to photo-labile pro-fragrances having the formula:

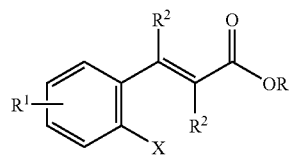

wherein —OR is a unit derived from a fragrance raw material alcohol, HOR; $R^1$ is one or more electron donating groups; each $R^2$ is independently hydrogen, $C_1$–$C_{12}$ alkyl, $C_7$–$C_{12}$ alkylenearyl; and mixtures thereof; X is selected from the group consisting of —OH, —$NH_2$, —$NHR^3$, and mixtures thereof; $R^3$ is hydrogen, $C_1$–$C_{12}$ linear or branched alkyl, $C_6$–$C_{10}$ aryl, $C_7$–$C_{12}$ alkylenearyl, and mixtures thereof.

The second aspect of the present invention relates to a fragrance raw material delivery system comprising:

i) from about 0.001% to about 100% by weight, of a photo-labile pro-fragrance compound having the formula:

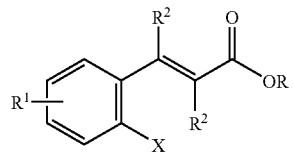

wherein R is a unit derived from a fragrance raw material alcohol; $R^1$ is one or more electron donating groups; each $R^2$ is independently hydrogen, $C_1$–$C_{12}$ alkyl, $C_7$–$C_{12}$ alkylenearyl; and mixtures thereof; X is selected from the group consisting of —OH, —$NHR^3$, and mixtures thereof; $R^3$ is H, $C_1$–$C_{12}$ alkyl, $C_7$–$C_{12}$ alkylenearyl, and mixtures thereof; and ii) optionally from about 0.001% to about 50% by weight, of one or more fragrance raw materials.

Another aspect of the present invention relates to personal care and laundry and cleaning compositions which comprise the fragrance delivery system of the present invention.

The present invention further relates to an aspect wherein in addition to the release of a fragrance raw material alcohol, the photo-labile trigger which is released can also itself be a fragrance raw material ingredient.

A further aspect of the present invention relates to methods for providing an enhanced duration or modified release fragrance.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to the surprising discovery that aryl acrylate pro-fragrances having the formula:

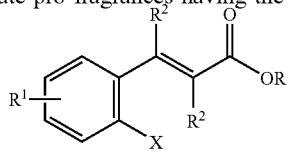

which are capable of releasing a fragrance raw material alcohol ROH, can be modified to have release half-lives which are useful to formulators and/or photo-fragment by-products which are useful to formulators.

The surprising discovery relates to the fact that $R^1$ units which are electron-donating groups, modulate the rate at which the photo-labile fragrance raw material is released. Without wishing to be limited by theory, the $R^1$ unit is capable of modulating the first photo-isomerization step and/or the second fragrance raw material elimination step.

The formulator can choose between combinations of $R^1$ and/or $R^2$ units to achieve the desired modulated release rate.

For the purposes of the present invention, the term "electron donating group" is defined herein as "functional groups which will tend to donate the electrons which comprise said groups toward another functional unit or bond, inter alia, aromatic rings, said donation of electrons referenced with respect to the propensity of a hydrogen atom to donate its electrons." Donating groups according to the present invention are —O⁻ (de-protonated hydroxy), —N($R^3$)$_2$, —NHR$^3$, —NH$_2$, —OH, —OR$^3$, —NHC(O)R$^3$, —NR$^3$C(O)R$^3$, —OC(O)R$^3$, —R$^3$, —CH=C($R^3$)$_2$, wherein $R^3$ is hydrogen, $C_1$–$C_{12}$ linear or branched alkyl, $C_6$–$C_{10}$ aryl, $C_7$–$C_{12}$ alkylenearyl, and mixtures thereof.

The first aspect of electron donating groups as it relates to the present invention comprise units defined herein as "strongly donating units" which are units selected from the group consisting of —O⁻ (de-protonated hydroxy), —N($R^3$)$_2$, —NHR$^3$, —NH$_2$, —OH, and —OR$^3$ wherein $R^3$ is $C_1$–$C_4$ alkyl.

The second aspect of electron donating groups as it relates to the present invention comprise units defined herein as "moderately/weakly donating units" which are units selected from the group consisting of —NHC(O)R$^3$, —NR$^3$C(O)R$^3$, —OC(O)R$^3$, —R$^3$, —CH=C($R^3$)$_2$, wherein $R^3$ is a $C_1$–$C_{12}$ linear or branched alkyl, phenyl, or benzyl.

However, for the purposes of the present invention, as indicated herein below, a strongly donating unit and a moderately/weakly donating unit may be contained in the same molecule.

The present invention also relates to the discovery that aryl acrylate pro-fragrances having the formula:

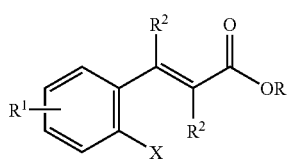

which are capable of releasing a fragrance raw material alcohol ROH and the photo-fragment by-product having the formula:

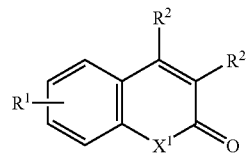

can be modified such that the photo-fragment by-product is a substituted coumarin derivative having an odor impact level especially useful to the formulators when combined with from about 0.001% to about 50% by weight of one or more fragrance raw materials. The discovery relates to the fact that $R^1$ units which are electron donating groups, as defined herein above, modulate the odor detection threshold level of the photo-fragment by-product that is released prior to or concomitant to the release of the photo-labile fragrance raw material.

Each $R^2$ is independently hydrogen, $C_1$–$C_{12}$ alkyl, $C_7$–$C_{12}$ alkylenearyl; and mixtures thereof. One embodiment of the present invention comprises each $R^2$ unit as a hydrogen, whereas other embodiments include alkyl, inter alia, methyl, and alkylenearyl, inter alia, benzyl.

Another embodiment relates to aryl acrylate pro-fragrances where the $R^1$ and $R^2$ units are chosen such that the coumarin derivative released from the aryl acrylate pro-fragrance has an odor detection threshold that is 2 times greater than the odor detection threshold for the corresponding coumarin derivative released from the aryl acrylate pro-fragrance where the $R^1$ and $R^2$ units are all chosen to be hydrogen.

For the purposes of the present invention X is —OH, —NH$_2$, or —NHR$^3$; whereas $X^1$ is the ring closed form of X, namely, —O—, —NH—, and —NR$^3$— respectively.

Without wishing to be limited by theory, the reaction cascade which releases the fragrance raw material alcohol of the present invention is believed to proceed as follows:

1. A first photo-isomerization step:

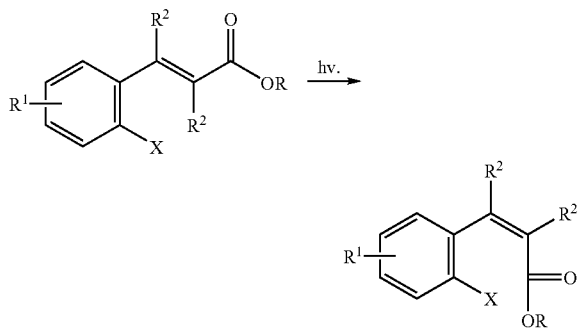

2. A second fragrance raw material elimination step:

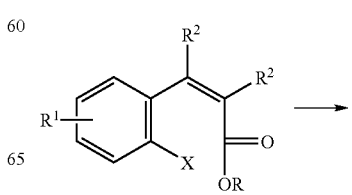

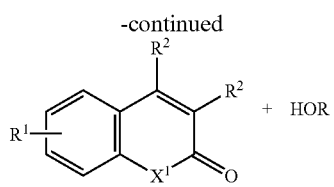

wherein R represents the released fragrance raw material alcohol.

One embodiment of the present invention relates to $R^1$ units which are hydroxy. One example of a pro-fragrance wherein X is hydroxy, an $R^1$ unit is also hydroxy, and both $R^2$ units are hydrogen relates to 3-(2,4-dihydroxyphenyl)-acrylate fragrance raw material esters having the formula:

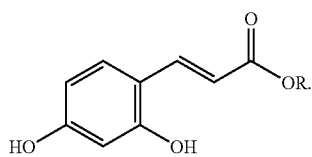

However, other embodiments include pro-fragrances having an $R^1$ hydroxy moiety in a ring position other than the 4-position, or to a pro-fragrance having multiple $R^1$ hydroxy units, for example, a pro-fragrance having the formula:

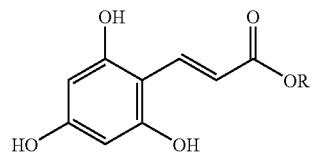

A further embodiment relates to $R^1$ units having the formula —$OR^3$ wherein $R^3$ is $C_1$–$C_{12}$ linear or branched alkyl or phenyl, for example, a pro-fragrance having the formula:

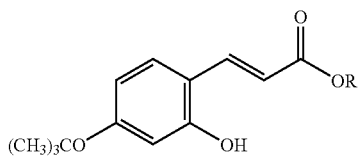

a pro-fragrance having the formula:

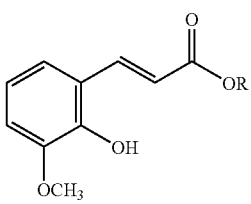

or a pro-fragrance having the formula:

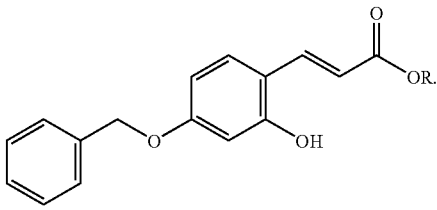

A further embodiment of the present invention relates to aryl rings substituted with one or more $C_1$–$C_{12}$ acyloxy units having the formula $R^3CO_2$—, for example, a pro-fragrance having the formula:

A further embodiment relates to $R^1$ units which are —$N(R^3)_2$ units wherein $R^3$ is hydrogen, $C_1$–$C_{12}$ linear or branched alkyl, or mixtures thereof, for example, a pro-fragrance having the formula:

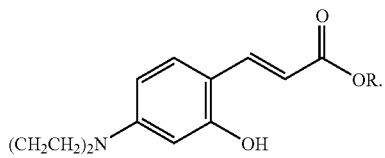

X units relate to aspects of the photo-labile pro-fragrances. A first aspect relates to X units which are —OH and which result in the formation of derivatives of coumarin as reaction by-products. A second aspect wherein X is —$NHR^3$ relates to the formation of derivatives of 2-hydroxyquinoline as reaction by-products. An example of a pro-fragrance wherein X is —$NH_2$, the $R^1$ unit is hydroxy, and both $R^2$ units are hydrogen relates to 3-(2-amino-4-hydroxyphenyl)-acrylate fragrance raw material esters having the formula:

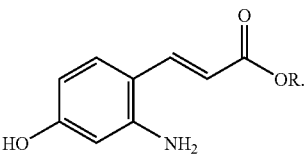

In both aspects of X, $R^2$ units can be units other than hydrogen, for example $C_1$ alkyl. One example of an embodiment wherein $R^2$ units are non-hydrogen is a pro-fragrance wherein X is hydroxy, each $R^1$ unit is hydrogen, one $R^2$ unit is methyl and the second $R^2$ unit is hydrogen is 3-(2-hydroxyphenyl)-3-methyl-acrylate fragrance raw material esters having the formula:

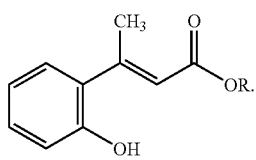

A further embodiment of the X equal to hydroxy aspect relates an $R^1$ units which is hydroxy and at least one $R^2$ unit which is alkyl. For example, 3-(2,4-dihydroxyphenyl)-3-methyl-acrylate having the formula:

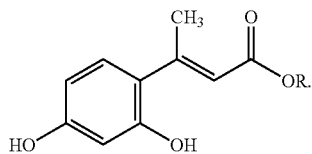

A third aspect of the present invention relates to the selection of $R^1$, $R^2$ and X units such that the rate of ROH fragrance raw material release is increased. One embodiment of this increased release selection relates to pro-fragrances releasing an ROH at a rate at least 1.5 times the rate of an analog having each $R^1$ and both $R^2$ units equal to hydrogen, also defined herein for X equal to hydroxy and amino as the "baseline" or "reference" analogs. Another aspect relates to a selection of moieties such that the rate of fragrance alcohol release is at least twice that rate of release by the corresponding baseline analog. A further embodiment increases the rate at least 3 times faster that the corresponding baseline analog.

R units are radicals derived from fragrance raw material alcohols. For the purposes of the present invention the term "fragrance raw material alcohol" is defined herein as "any alcohol having a molecular weight of 100 g/mole or greater."

For the purposes of the present invention fragrance raw material alcohols are grouped into classes, for example, alcohols which comprise nearly the same structure will have comparable release rates with the same electron donating $R^1$. A non-limiting example of these similar alcohols include geraniol and nerol which are isomers.

For the purposes of the present invention the following are defined herein as fragrance raw materials alcohols derived from a terpene: geraniol, nerol, eugenol, isoeugenol, citronellol, menthol, isopulegol, terpineol, borneol, isoborneol, linalool, tetrahydrolinalool, myrcenol, dihydromyrcenol, muguol, farnesol and mixtures thereof. However, the formulator will realize these are not the only terpene raw material alcohols but are those which comprise one embodiment of the present invention.

Non-limiting examples of R units derived from a non-terpene alcohol include those selected from the group consisting of cinnamyl alcohol, methylcinnamyl alcohol, Majantol, Hydrotropic alcohol, nopol, Lavandulol, carvenol, cuminyl alcohol, thymol, and mixtures thereof.

For the purposes of the present invention, the following are defined herein as "blossom alcohols": 4-(1-methylethyl)cyclo-hexanemethanol, 2,4-dimethyl-3-cyclohexen-1-yl-methanol, 2,4-dimethylcyclohex-1-ylmethanol, 2,4,6-trimethyl-3-cyclohexen-1-ylmethanol, 2-phenylethanol, 1-(4-isopropylcyclohexyl)ethanol, 2-(o-methylphenyl)ethanol, 2-(m-methylphenyl)ethanol, 2-(p-methylphenyl)-ethanol, 2,2-dimethyl-3-(3-methylphenyl)propan-1-ol, 3-phenyl-2-propen-1-ol, 2-methyl-4-(2,2,3-trimethyl-3-cyclopenten-1-yl)-2-buten-1-ol, 3-methyl-5-phenylpentan-1-ol, 3-methyl-5-(2,2,3-trimethyl-3-cyclopenten-1-yl)-4-penten-2-ol, 2-methyl-4-phenylpentan-1-ol, cis-3-hexen-1-ol, 3,7-dimethyl-6-octen-1-ol, 3,7-dimethyl-2,6-octadien-1-ol, 7-methoxy-3,7-dimethyloctan-2-ol, 6,8-dimethylnonan-2-ol, cis-6-nonen-1-ol, 2,6-nonadien-1-ol, 4-methyl-3-decen-5-ol, benzyl alcohol, 2-methoxy-4-(1-propenyl)phenol, 2-methoxy-4-(2-propenyl)phenol, 4-hydroxy-3-methoxybenzaldehyde, and mixtures thereof.

Fragrance raw material alcohols suitable for use in the present invention are described in U.S. Pat. No. 5,919,752 Morelli et al., issued Jul. 6, 1999; U.S. Pat. No. 6,013,618 Morelli et al., issued Jan. 11, 2000; U.S. Pat. No. 6,077,821 Morelli et al., issued Jun. 20, 2000; U.S. Pat. No. 6,087,322 Morelli et al., issued Jul. 11, 2000; U.S. Pat. No. 6,114,302 Morelli et al., issued Sep. 5, 2000; U.S. Pat. No. 6,177,389 Morelli et al., issued Jan. 23, 2001; all of which are incorporated herein by reference.

The present invention further relates to an aspect wherein in addition to the release of a fragrance raw material alcohol, the photo-labile trigger which is released can also itself be a fragrance raw material ingredient. For example, the material released by the X equals oxygen aspect (coumarin derivatives) may itself be a fine fragrance component, fragrance raw material, or perfume adjunct ingredient. The same is equally true for the X equals nitrogen aspect (2-hydroxyquinoline derivatives).

Or in another embodiment, the coumarin derivative which is release may provide a different benefit, for example, once the ring closure reaction is complete, the resulting compound may have sufficient conjugation to be a colored material, and therefore serve as a visual signal.

The following relates to methods for preparing the photo-labile pro-fragrances of the present invention.

A first procedure relates to the conversion of a starting material having formula 1 to the aryl acrylate photo-labile pro-fragrance 3 by way of the intermediate aryl acrylic acid 2 as depicted in the following scheme:

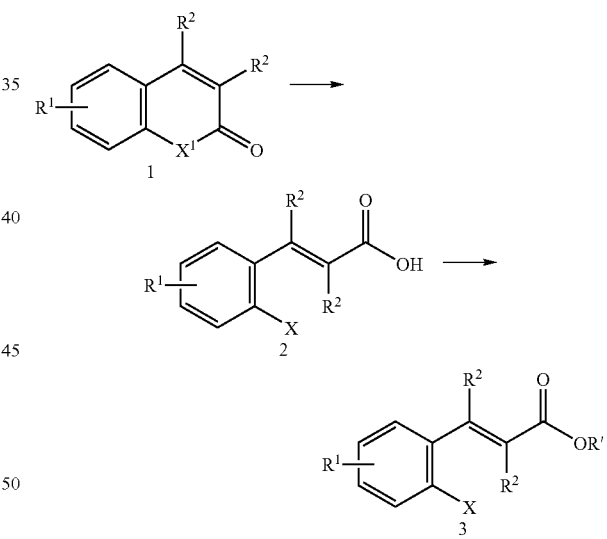

In the case wherein X is equal to oxygen (coumarin derivatives) the preparation begins with a von Pechmann condensation as in the example of the reaction of recorcinol with acetoacetic acid ethyl ester depicted in the following scheme:

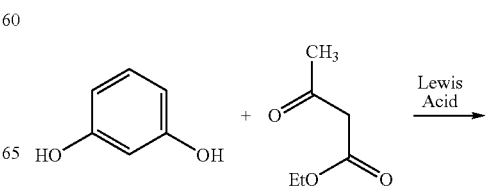

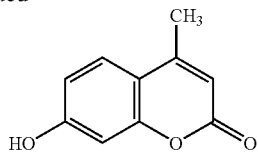

Coumarin syntheses are reviewed by Dean, F. M. "Naturally Occurring Oxygen Ring Compounds"; Butterworths: London, 1963; p. 176.

EXAMPLE 1

3-(2,4-Dihydroxyphenyl)acrylic acid 1,5-dimethyl-1-vinylhex-4-enyl ester

Step (1) preparation of 3-(2,4-dihydroxyphenyl)acrylic acid (5) from 7-hydroxy-chromen-2-one (4):

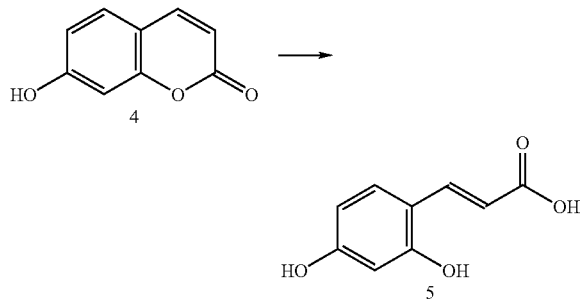

To a solution of 20% sodium sulfite (640 g) at 60° C. is added 7-hydroxychromen-2-one (75.0 g, 0.416 mol). The reaction mixture is warmed to 100° C. and stirred for 1.5 h. To this solution is added dropwise 30% KOH solution (301 g). The stirred mixture is cooled to 0° C. and acidified by the slow and careful addition of concentrated HCl, keeping the solution temperature below 10° C. The colorless precipitate is separated by filtration, washed with water and dried for 12 h under vacuum at 45° C. The resulting 3-(2,4-dihydroxyphenyl)-acrylic acid is a colorless solid (24.0 g) and is used without further purification.

Step (2) preparation of 3-(2,4-Dihydroxyphenyl)-acrylic acid 1,5-dimethyl-1-vinyl-hex-4-enyl ester (6) from 3-(2,4-dihydroxyphenyl)acrylic acid (5).

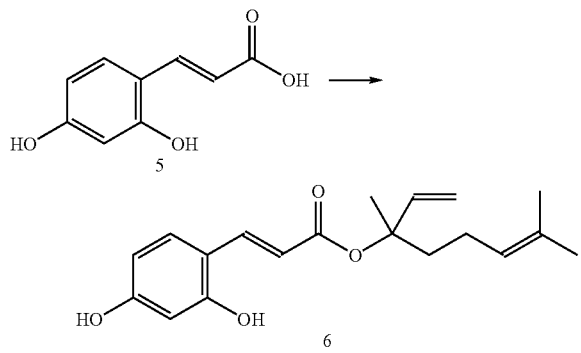

To a solution of linalool (1.74 g, 11.3 mmol) and triethylamine (2.30 g, 22.6 mmol) in anhydrous THF (150 mL) stirred for 5 min at 22° C. is added 3-(2,4-dihydroxyphenyl)-acrylic acid (2.04 g, 11.3 mmol). To this heterogeneous solution is added BOP Reagent (5.00 g, 11.3 mmol; Aldrich #22,608-4) in DMF (10 mL), and the subsequent homogeneous reaction mixture is stirred for 1 h. The reaction mixture is partitioned between ether (200 mL) and water (400 mL); the organic layer is removed and washed with ether (200 mL). The combined organic layers are washed sequentially with saturated sodium bicarbonate solution (200 mL) and brine (200 mL). The organic layer is dried over anhydrous magnesium sulfate, vacuum filtered and concentrated to give 3-(2,4-dihydroxyphenyl)-acrylic acid 1,5-dimethyl-1-vinyl-hex-4-enyl ester as an oil that is purified by flash chromatography.

EXAMPLE 2

(E)-3-(2,4-dihydroxyphenyl)-but-2-enoic acid phenethyl ester (E)-3-(2,4-dihydroxyphenyl)-but-2-enoic acid phenethyl ester (8) from 3-(2,4-dihydroxyphenyl)-but-2-enoic acid (7):

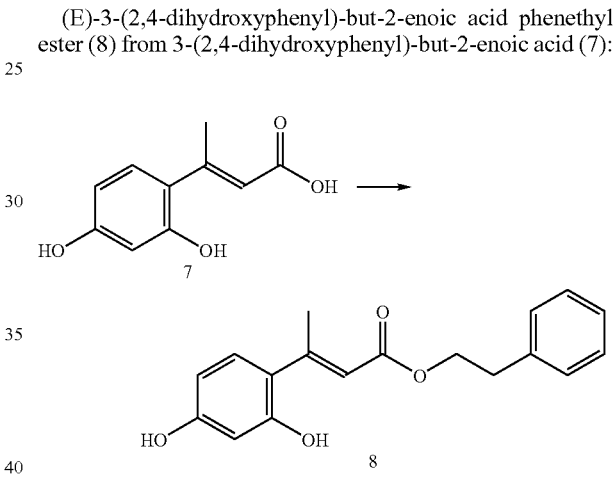

To a 0° C. solution of 9.7 g (0.050 mol) of 3-(2,4-dihydroxyphenyl)but-2-enoic acid in 500 mL of anhydrous tetrahydrofuran (THF) is added 10.3 g (0.050 mol) of 1,3-dicyclohexylcarbodiimide (DCC). After stirring for 10 min, 6.8 g (0.050 mol) of 1-hydroxybenzotriazole (HOBt), 5.5 g (0.045 mol) of phenethyl alcohol and 1.1 g (0.009 mol) of 4-(dimethylamino)pyridine (DMAP) is added and stirred at 0° C. for 1 h, warmed to 22° C. and stirred for an additional 72 h. The mixture is cooled to 0° C., filtered and the solvent is removed under vacuum. The residue is diluted with ethyl acetate and washed three times with saturated sodium bicarbonate, followed by 10% citric acid and brine. The organic layer is dried over anhydrous magnesium sulfate, filtered and concentrated under vacuum to give (E)-3-(2,4-dihydroxyphenyl)-but-2-enoic acid phenethyl ester as a yellow oil that is purified by flash chromatography.

EXAMPLE 3

3-(3-Benzoyl-2,4-dihydroxyphenyl)but-2-enoic acid 3,7-dimethyloct-7-enyl ester

8-Benzoyl-7-hydroxy-4-methylchromen-2-one (9) is prepared according to Chem. Ber. 1934, 67, 12, included herein by reference.

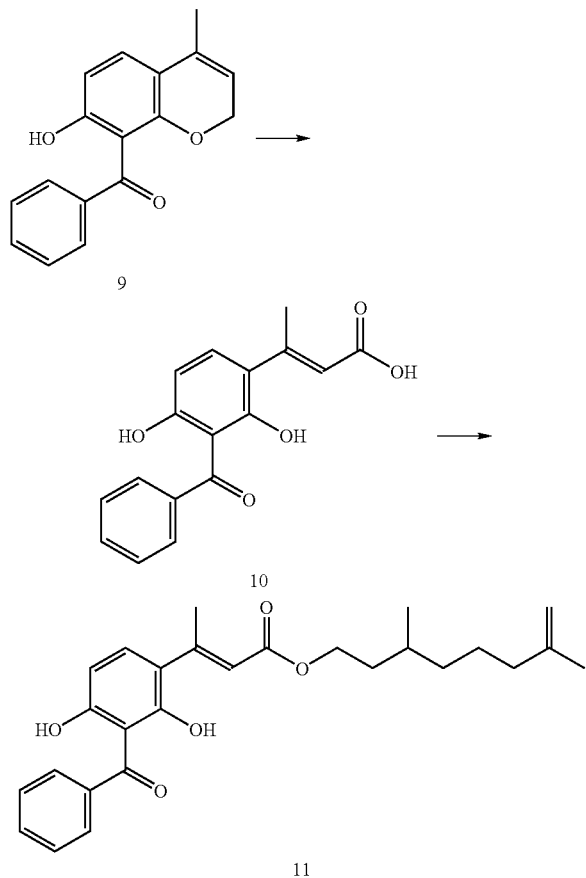

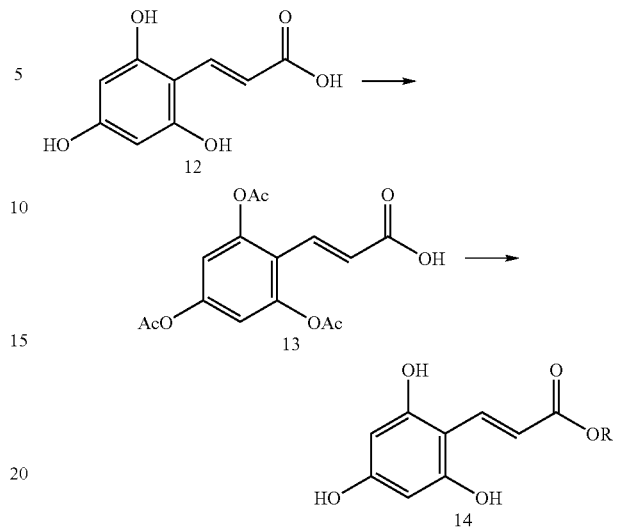

The procedure used in Step (1) of Example 1 can be used to convert starting material 9 to intermediate 10.

A solution of 3-(3-benzoyl-2,4-dihydroxyphenyl)-but-2-enoic acid (5.97 g, 20.0 mmol), citronellol (3.13 g, 20.0 mmol) and p-toluenesulfonic acid (1 g) in cyclohexane (150 mL) is refluxed for 6 h under vacuum using a Dean Stark separator. The reaction mixture is partitioned between methylene chloride (150 mL) and water (150 mL); the organic layer is removed and washed with methylene chloride (100 mL). The combined organic layers are washed sequentially with saturated sodium bicarbonate solution (100 mL) and brine (100 mL). The organic layer is dried over anhydrous magnesium sulfate, filtered and concentrated to give (E)-3-(3-benzoyl-2,4-dihydroxyphenyl)-but-2-enoic acid 3,7-dimethyl-oct-7-enyl ester as an oil which can be purified by flash chromatography.

EXAMPLE 4

3-(2,4-trihydroxyphenyl)-acrylic acid 3,7-dimethylocta-2,6-dienyl ester

Step (1) which is conversion of starting material 12 to intermediate 13 can be a accomplished by the method described in *Synthetic Comm.* 1991, 21, 351 included herein by reference.

Step (2) conversion of intermediate 13 3-(2,4,6-trihydroxyphenyl)-acrylic acid 3,7-dimethylocta-2,6-dienyl ester 14.

A solution of intermediate 13 (1.20 g, 3.7 mmol), thionyl chloride (2 equiv, 0.88 g, 7.4 mmol, 0.54 mL) in anhydrous toluene (50 mL) is refluxed for 3 h under an inert atmosphere. The reaction mixture is evaporated to dryness under vacuum and to the crude acid chloride is added another portion of toluene (50 mL). Geraniol (0.57 g, 3.7 mmol) is added and the reaction mixture is allowed to stir for 12 h. The mixture is diluted with toluene (100 mL) and washed with 100 mL portions of 1 N HCl, water and brine. The organic layer is dried over anhydrous magnesium sulfate, filtered and concentrated to give 3-(2,4,6-triacetoxy-phenyl)-acrylic acid 3,7-dimethyl-octa-2,6-dienyl ester. Removal of the acetoxy units by the method of *Synthetic Comm.* 1991, 21, 351, incorporated herein by reference, affords 3-(2,4,6-trihydroxyphenyl)-acrylic acid 3,7-dimethyl-octa-2,6-dienyl ester.

FRAGRANCE DELIVERY SYSTEM

The present invention relates to a fragrance delivery system for providing an enhanced and enduring fragrance aesthetic benefit using the photo-labile pro-fragrances described herein above.

The first aspect of the delivery systems relates to systems comprising:

i) from about 0.001% to about 100%, in another embodiment from about 0.002% to about 20% by weight, of a photo-labile pro-fragrance compound described herein above; and ii) optionally from about 0.005% to about 50% by weight, of one or more fragrance raw materials.

In one embodiment of this aspect, an amount of pro-fragrance is admixed with a fragrance raw material and/or pro-perfume, and the release rates are adjusted such that the amount of fragrance raw material which is released is capable of replenishing any originally formulated fragrance raw material thereby sustaining about the same relative concentration of fragrance raw material.

The fragrance raw materials which are suitable for optional incorporation into the systems of the present invention are also defined in the herein above incorporated references, as well as P. M. Muller, D. Lamparsky *Perfumes Art, Science, & Technology* Blackie Academic & Professional, (New York, 1994); and *Perfume and Flavor Chemicals*, Vols. I and II; Steffen Arctander Allured Pub. Co. (1994) both of which are included herein by reference.

One embodiment of the present invention relates to a system comprising:
i) from about 0.001% to about 90% by weight, of a photo-labile pro-fragrance compound described herein above;
ii) from about 0.005% to about 50% by weight, of one or more fragrance raw materials alcohols which are released by said photo-labile pro-fragrance; and
iii) the balance a carrier.

In addition, another aspect of the present invention relates to systems comprising:
i) from about 0.001% to about 99% by weight, of a photo-labile pro-fragrance compound described herein above;
ii) from about 0.01% to about 50% by weight, of one or more fragrance raw materials; and
iii) the balance a carrier.

Another aspect of the present invention relates to fragrance delivery systems which comprise a combination of photo-labile and non-photo-labile pro-fragrances, said system comprising:
i) from about 0.001% to about 99.9% by weight, of a photo-labile pro-fragrance compound described herein above;
ii) from about 0.001% to about 99.9% by weight, of one or more non-photo-labile pro-fragrances selected from the group consisting of cyclic animals (including oxazolidines and tetrahydro oxazines), β-aminoketones, acetals, ketals, esters, β-ketoesters, orthoesters, orthocarbonates, and mixtures thereof;
iii) fragrance raw materials alcohols which are released by said photo-labile pro-fragrance; and
iv) the balance a carrier.

FORMULATIONS

The fragrance delivery systems of the present invention are suitable for use in any laundry detergent matrix, for example, granular, paste, agglomerates, tablets liquids, and the like.

One aspect of the present invention relates to liquid laundry detergent compositions which provide a stable, flowable liquid matrix. One aspect of the present invention relates to compositions comprising:
a) from about 0.001% to about 10% by weight, of one or more photo-labile pro-fragrance compound described herein above;
b) from about 10% by weight, in one embodiment from about 10% to about 80% by weight, in yet another embodiment from about 10% to about 60%, wherein another embodiment comprises from about 15% to about 30% by weight, of a surfactant system, said surfactant system comprising:
 i) from 0.01%, whereas depending upon which aspect or embodiment of the present invention, the following ranges are suitable: from about 0.1% to about 100%; from about 1% to about 80%; from about 1% to about 60%, from about 1% to about 30% by weight, of one or more anionic surfactants, said anionic surfactants selected form the group consisting of linear alkyl benzene sulphonates, mid-chain branched alkyl benzene sulphonates; linear alkyl sulfates, mid-chain branched sulfates, linear alkyleneoxy sulfates, mid-chain branched alkyleneoxy sulfates; and mixtures thereof;
 ii) optionally, from 0.01%, whereas depending upon which aspect or embodiment of the present invention, the following ranges are suitable: from about 0.1% to about 100%; from about 1% to about 80%; from about 1% to about 60%, from about 1% to about 30% by weight, of one or more nonionic surfactants selected from the group consisting of alcohols, alcohol ethoxylates, polyoxyalkylene alkylamides, and mixtures thereof; and
c) the balance carriers and other adjunct ingredients.

When the liquid detergent compositions of the present invention are used, the pH of the resulting aqueous solution, upon dilution, will have a value of from about 7 to about 8.5. One embodiment of the present invention has a wash water pH during use of about 8.

Formulations according to the present invention may comprise a dispersant system which comprises one or more dispersants, said system including one or more hydrophobic soil dispersants according to the present invention. Said mixed dispersant compositions comprise:
a) from about 0.01% to about 10% by weight, of said detergent composition, a fragrance delivery system, said system comprising:
 i) from about 0.01% to about 90% by weight, of a photo-labile pro-fragrance compound described herein above;
 ii) from about 0.01% to about 50% by weight, of one or more fragrance raw materials alcohols which are released by said photo-labile pro-fragrance; and
 iii) the balance a carrier;
b) from about 10% by weight, in one embodiment from about 10% to about 80% by weight, in yet another embodiment from about 10% to about 60%, wherein another embodiment comprises from about 15% to about 30% by weight, of a surfactant system according to the present invention; and
c) the balance carriers and other adjunct ingredients.

One embodiment of this aspect of the present invention comprises:
a) from about 0.01% to about 5% by weight, of said liquid laundry detergent composition, a fragrance delivery system, said dispersant system comprising:
 i) from about 0.001% to about 99.9% by weight, of a photo-labile pro-fragrance compound described herein above;
 ii) from about 0.001% to about 99.9% by weight, of one or more non-photo-labile pro-fragrances selected from the group consisting of acetals, ketals, esters, β-ketoesters, orthoesters, orthocarbonates, and mixtures thereof;
 iii) fragrance raw materials alcohols which are released by said photo-labile pro-fragrance; and
 iv) the balance a carrier.

SURFACTANT SYSTEM

The laundry detergent compositions of the present invention comprise a surfactant system. The surfactant systems of the present invention may comprise any type of detersive surfactant, non-limiting examples of which include one or more mid-chain branched alkyl sulfate surfactants, one or more mid-chain branched alkyl alkoxy sulfate surfactants, one or more mid-chain branched aryl sulfonate surfactants, one or more non mid-chain branched sulphonates, sulphates, cationic surfactants, zwitterionic surfactants, ampholytic surfactants, and mixtures thereof.

The total amount of surfactant present in the compositions of the present invention is from about 10% by weight, in one embodiment of the present invention the range of surfactant is from about 10% to about 80% by weight, of said composition. Another embodiment the amount of surfactant is from about 10% to about 60%, wherein another embodiment comprises from about 15% to about 30% by weight, of said composition.

Nonlimiting examples of surfactants useful herein include:

a) $C_{11}$–$C_{18}$ alkyl benzene sulfonates (LAS);
b) $C_6$–$C_{18}$ mid-chain branched aryl sulfonates (BLAS);
c) $C_{10}$–$C_{20}$ primary, α or ω-branched, and random alkyl sulfates (AS);
d) $C_{14}$–$C_{20}$ mid-chain branched alkyl sulfates (BAS);
e) $C_{10}$–$C_{18}$ secondary (2,3) alkyl sulfates as described in U.S. Pat. No. 3,234,258 Morris, issued Feb. 8, 1966; U.S. Pat. No. 5,075,041 Lutz, issued Dec. 24, 1991; U.S. Pat. No. 5,349,101 Lutz et al., issued Sep. 20, 1994; and U.S. Pat. No. 5,389,277 Prieto, issued Feb. 14, 1995 each incorporated herein by reference;
f) $C_{10}$–$C_{18}$ alkyl alkoxy sulfates ($AE_xS$) wherein preferably x is from 1–7;
g) $C_{14}$–$C_{20}$ mid-chain branched alkyl alkoxy sulfates ($BAE_xS$);
h) $C_{10}$–$C_{18}$ alkyl alkoxy carboxylates preferably comprising 1–5 ethoxy units;
i) $C_{12}$–$C_{18}$ alkyl ethoxylates, $C_6$–$C_{12}$ alkyl phenol alkoxylates wherein the alkoxylate units are a mixture of ethyleneoxy and propyleneoxy units, $C_{12}$–$C_{18}$ alcohol and $C_6$–$C_{12}$ alkyl phenol condensates with ethylene oxide/propylene oxide block polymers inter alia Pluronic® ex BASF which are disclosed in U.S. Pat. No. 3,929,678 Laughlin et al., issued Dec. 30, 1975, incorporated herein by reference;
j) $C_{14}$–$C_{22}$ mid-chain branched alkyl alkoxylates, $BAE_x$;
k) Alkylpolysaccharides as disclosed in U.S. Pat. No. 4,565,647 Llenado, issued Jan. 26, 1986, incorporated herein by reference;
l) Pseudoquat surfactants having the formula:

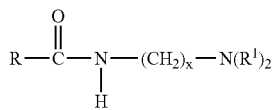

wherein R is $C_4$–$C_{10}$ alkyl, $R^1$ is selected from the group consisting of $C_1$–$C_4$ alkyl, —$(CH_2CHR^2O)_yH$, and mixtures thereof; $R^2$ is hydrogen, ethyl, methyl, and mixtures thereof; y is from 1 to 5; x is from 2 to 4; for the purposes of the present invention, a particularly useful pseudoquat surfactant comprises R equal to an admixture of $C_8$–$C_{10}$ alkyl, $R^1$ is equal to methyl; and x equal to 3; these surfactants are described in U.S. Pat. No. 5,916,862 Morelli et al., issued Jun. 29, 1999 included herein by reference;
m) Polyhydroxy fatty acid amides having the formula:

wherein $R^7$ is $C_5$–$C_{31}$ alkyl; $R^8$ is selected from the group consisting of hydrogen, $C_1$–$C_4$ alkyl, $C_1$–$C_4$ hydroxyalkyl, Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof. These surfactants are described in U.S. Pat. No. 5,489,393 Connor et al., issued Feb. 6, 1996; and U.S. Pat. No. 5,45,982 Murch et al., issued Oct. 3, 1995, both incorporated herein by reference.

The mid-chain branched alkyl sulfate surfactants of the present invention have the formula:

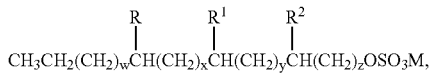

the alkyl alkoxy sulfates have the formula:

the alkyl alkoxylates have the formula:

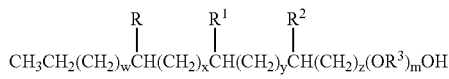

wherein R, $R^1$, and $R^2$ are each independently hydrogen, $C_1$–$C_3$ alkyl, and mixtures thereof; provided at least one of R, $R^1$, and $R^2$ is not hydrogen; preferably R, $R^1$, and $R^2$ are methyl; preferably one of R, $R^1$, and $R^2$ is methyl and the other units are hydrogen. The total number of carbon atoms in the mid-chain branched alkyl sulfate and alkyl alkoxy sulfate surfactants is from 14 to 20; the index w is an integer from 0 to 13; x is an integer from 0 to 13; y is an integer from 0 to 13; z is an integer of at least 1; provided w+x+y+z is from 8 to 14 and the total number of carbon atoms in a surfactant is from 14 to 20; $R^3$ is $C_1$–$C_4$ linear or branched alkylene, preferably ethylene, 1,2-propylene, 1,3-propylene, 1,2-butylene, 1,4-butylene, and mixtures thereof.

M denotes a cation, preferably hydrogen, a water soluble cation, and mixtures thereof. Non-limiting examples of water soluble cations include sodium, potassium, lithium, ammonium, alkyl ammonium, and mixtures thereof.

The following are non-limiting examples of shampoo compositions according to the present invention.

TABLE I

| Ingredients | weight % | | | |
| --- | --- | --- | --- | --- |
|  | 5 | 6 | 7 | 8 |
| Ammonium laureth-3 sulfate | 10.00 | 10.00 | 10.00 | 10.00 |
| Ammonium lauryl sulfate | 6.00 | 2.00 | 2.00 | 2.00 |
| Cocamidopropyl betaine FB | — | 2.00 | 2.00 | 2.00 |
| Sodium lauraoamphoacetate | — | 2.00 | 2.00 | 2.00 |
| Cetyl alcohol | 0.90 | 0.60 | 0.60 | 0.60 |
| Cocamide MEA | 0.80 | 0.80 | 0.80 | 0.80 |
| Polyquat 10[1] | 0.50 | 0.50 | 0.50 | 0.50 |
| Ethylene glycol distearate | 1.50 | 1.50 | 0.75 | 1.50 |
| Dimethicone[2] | 2.00 | — | — | — |
| Dimethicone[3] | — | 2.00 | 1.00 | 1.00 |
| PPG 15 stearyl ether[4] | 2.00 | 2.00 | 2.00 | 2.00 |
| Mobil P43 synthetic oil[5] | 0.10 | — | — | — |

TABLE I-continued

| Ingredients | weight % | | | |
|---|---|---|---|---|
| | 5 | 6 | 7 | 8 |
| Puresyn 6 (MCP-1812)[6] | 0.40 | — | — | 0.25 |
| Perfume solution[7] | 0.70 | 0.70 | 0.70 | 0.70 |
| Sodium citrate | 0.40 | 0.40 | 0.40 | 0.40 |
| Citric acid | 0.04 | 0.40 | 0.40 | 0.40 |
| Ammonium xylene sulfonate | — | 1.70 | 1.50 | 1.50 |
| Sodium chloride | 0.50 | — | — | — |
| Pro-fragrance[8] | 1.00 | 1.00 | 1.25 | 0.50 |
| Water/Carriers/aesthetics | balance | balance | balance | balance |

[1]Polymer KG30M available ex Amerchol/Dow Chemical.
[2]Viscasil 330M available from General Electric Silicones.
[3]DC 1664 available from Dow Corning Silicones.
[4]Arlamol E available ex Uniquema.
[5]P43 oil available ex Exxon/Mobil Chemical.
[6]Puresyn 6 available from Exxon/Mobil Chemical.
[7]Admixture of perfume raw materials.
[8]According to Example 1

TABLE II

| Ingredients | weight % | | | |
|---|---|---|---|---|
| | 9 | 10 | 11 | 12 |
| Ammonium laureth-3 sulfate | 10.00 | 11.70 | 10.00 | 10.00 |
| Ammonium lauryl sulfate | 5.00 | 2.30 | 2.00 | 2.00 |
| Cocamidopropyl betaine FB | — | — | 2.00 | 2.00 |
| Sodium lauroamphoacetate | — | — | 2.00 | 2.00 |
| Cocaminopropionic acid | 3.00 | 2.00 | — | — |
| Cetyl alcohol | 0.90 | 0.60 | 0.60 | 0.60 |
| Cocamide MEA | 0.80 | 0.80 | 0.80 | 0.80 |
| Polyquat 10[1] | 0.50 | 0.50 | 0.50 | 0.50 |
| Ethylene glycol distearate | 1.50 | 1.50 | 0.75 | 1.50 |
| Dimethicone[2] | 2.00 | 2.00 | 2.00 | 2.00 |
| PPG 15 stearyl ether[3] | 2.00 | 2.00 | 1.00 | 2.00 |
| Varisoft CB110[4] | — | — | — | 0.15 |
| Perfume solution[5] | 0.70 | 0.70 | 0.70 | 0.70 |
| Sodium citrate | 0.40 | 0.40 | 0.40 | 0.40 |
| Citric acid | 0.04 | 0.40 | 0.40 | 0.40 |
| Ammonium xylene sulfonate | — | 1.70 | 1.50 | 1.50 |
| Sodium chloride | 0.50 | — | — | — |
| Pro-fragrance[6] | 1.00 | 1.00 | 1.25 | 0.50 |
| Water/Carriers/aesthetics | balance | balance | balance | balance |

[1]Polymer KG30M available ex Amerchol/Dow Chemical.
[2]Viscasil 330M available from General Electric Silicones.
[3]DC 1664 available from Dow Corning Silicones.
[4]Varisoft CB110 available from Witco/Degussa.
[5]Admixture of perfume raw materials.
[6]According to Example 1

TABLE III

| Ingredients | weight % | | | |
|---|---|---|---|---|
| | 13 | 14 | 15 | 16 |
| $C_{12}$–$C_{15}$ alkyl $E_{1.1}$ sulfate | 18.0 | 14.4 | 18.0 | — |
| Linear alkyl benzene sulphonate | 2.40 | 4.44 | 5.8 | 15 |
| $C_{12}$–$C_{13}$ alkyl alcohol | 2.40 | 2.22 | 2.8 | 8.4 |
| $C_{10}$–$C_{12}$ alkyl psuedo quat.[1] | 1.20 | — | — | — |
| $C_8$–$C_{10}$ APA | — | — | 1.4 | 1.4 |
| Amine oxide | — | 0.74 | — | — |
| Citric acid | 2.80 | 2.59 | 2.5 | 1.0 |
| $C_{12}$–$C_{18}$ alkyl fatty acid[2] | 3.20 | 2.96 | 5.0 | 10 |
| Enzymes | 3.77 | 2.83 | 3.25 | 3.25 |
| Chelant[3] | 0.15 | 0.15 | 0.15 | 0.15 |
| Photo-labile pro-fragrance[4] | 0.22 | 0.025 | 1.5 | 0.005 |
| Pro-fragrance | 1.00 | — | — | — |

TABLE III-continued

| Ingredients | weight % | | | |
|---|---|---|---|---|
| | 13 | 14 | 15 | 16 |
| Perfume raw material | 0.20 | 0.25 | 1.2 | 0.050 |
| Water/Carriers/aesthetics | balance | balance | balance | balance |

[1]According to U.S. Pat. No. 5,916,862 Morelli et al., issued Jun. 29, 1999.
[2]From topped palm kernel oil.
[3]Diethylenetriamine pentaacetate.
[4]According to Example 1.

The following are non-limiting examples of a light duty liquid dishwashing detergent according to the present invention.

TABLE IV

| Ingredients | weight % | | | |
|---|---|---|---|---|
| | 17 | 18 | 19 | 20 |
| $C_{12}$–$C_{14}$ alkyl $E_{1.4}$ sulfate | 24.69 | 33.50 | 34.20 | — |
| $C_{12}$–$C_{14}$ alkyl $E_{2.2}$ sulfate | — | — | — | 28.80 |
| Glucose amide[1] | 3.09 | 6.00 | 4.20 | 1.43 |
| $C_{12}$–$C_{14}$ alkyl dimethyl N-oxide | 2.06 | 6.00 | 4.81 | 4.94 |
| $C_{12}$ dimethyl carboxymethyl amine[2] | 2.06 | — | — | — |
| $C_{10}$ $E_8$ alcohol | 4.11 | — | — | — |
| $C_{11}$ $E_9$ alcohol | — | 1.00 | 1.00 | 0.95 |
| Magnesium[3] | 0.49 | 0.80 | 0.72 | 0.68 |
| Calcium[4] | — | 0.40 | 0.35 | 0.33 |
| Ethanol | 7.50 | 5.00 | 5.25 | 5.85 |
| Hydrotrope[5] | 4.47 | 4.00 | 3.50 | 4.75 |
| Photo-labile pro-fragrance[6] | 0.50 | 0.25 | 0.035 | 1.25 |
| Pro-fragrance | — | — | — | 0.10 |
| Perfume raw material | 1.20 | 0.75 | 0.25 | — |
| Carriers/aesthetics | balance | balance | balance | balance |
| Viscosity (cps) | 150 | 300 | 300 | 300 |
| pH of a 10% aqueous solution | 7.8 | 7.8 | 7.4 | 7.4 |

[1]$C_{12}$–$C_{14}$ alkyl $C_6$ glucosamine amide.
[2]Betaine surfactant.
[3]As $Mg^{2+}$.
[4]As $Ca^{2+}$.
[5]For example, sodium cumene sulphonate.
[6]According to Example 1.

The laundry detergent compositions of the present invention can be suitably prepared by any process chosen by the formulator, non-limiting examples of which are described in U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996 all of which are incorporated herein by reference.

A personal care cleanser composition is prepared by combining the following ingredients using conventional mixing techniques.

TABLE V

| Ingredients | Weight % | | | |
|---|---|---|---|---|
| | 21 | 22 | 23 | 24 |
| Phase A | | | | |
| Water | QS 100 | QS 100 | QS 100 | QS 100 |
| Disodium EDTA | 0.100 | 0.100 | 0.100 | 0.100 |
| Glycerin | 4.00 | 4.00 | 4.00 | 4.00 |

TABLE V-continued

| | Weight % | | | |
|---|---|---|---|---|
| Ingredients | 21 | 22 | 23 | 24 |
| Methylparaben | 0.200 | 0.200 | 0.200 | 0.200 |
| C₁₀–C₃₀ alkyl acrylate crosspolymer¹ | 0.150 | 0.150 | 0.150 | 0.150 |
| Carbomer 954² | 0.250 | 0.250 | 0.250 | 0.250 |
| Phase B | | | | |
| Stearic Acid | 0.110 | 0.110 | 0.110 | 0.110 |
| Stearyl alcohol | 0.875 | 0.875 | 0.875 | 0.875 |
| Cetyl alcohol | 0.875 | 0.875 | 0.875 | 0.875 |
| Propylparaben | 0.150 | 0.150 | 0.150 | 0.150 |
| Steareth-2 | — | 0.25 | 0.25 | 0.25 |
| Steareth-21 | — | 0.50 | 0.50 | 0.50 |
| Phase C | | | | |
| Sodium hydroxide³ | 0.130 | 0.130 | 0.130 | 0.130 |
| Phase D | | | | |
| Diisopropyl sebacate | 1.50 | 1.50 | 1.50 | 1.50 |
| Isohexadecane | 5.00 | 2.00 | 5.00 | 5.00 |
| Mineral Oil⁴ | — | 5.00 | — | — |
| Phase E | | | | |
| Phenoxyethanol | 0.5 | 0.5 | — | 0.5 |
| Photo-labile pro-fragrance⁵ | 0.75 | 0.90 | 1.00 | 1.25 |
| Pro-accord⁶ | — | — | 2.20 | 0.50 |
| Perfume raw material | 1.0 | 0.20 | 3.0 | 1.5 |
| Phase F | | | | |
| Glucose amide | 0.96 | 0.96 | 0.96 | 0.96 |

¹Available as Pemulen ® from B. F. Goodrich Corporation.
²Available as Carbomer ® 954 from B. F. Goodrich Corporation.
³As a 50% aqueous solution.
⁴Light mineral oil available as Drakeol 5 from Penreco, Dickenson, TX.
⁵According to Example 1.
⁶Fragrance pro-accord admixture comprising 75% tris(phenylethyl) orthoacetate and 25% tris(cis-3-hexenyl) orthoformate.

The above Examples 13–16 can be suitably prepared as follows. In a suitable vessel, the Phase A ingredients are mixed at room temperature to form a dispersion and heated with stirring to 70–80° C. In a separate vessel, the Phase B ingredients are heated with stirring to 70–80° C. Phase B is then added to Phase A with mixing to form the emulsion. Next, Phase C is added to neutralize the composition. The Phase D ingredients are added with mixing, followed by cooling to 45–50° C. The Phase E ingredients are then added with stirring, followed by cooling to 40° C. Phase F is heated with mixing to 40° C. and added to the emulsion, which is cooled to room temperature. The resulting cleansing composition is useful for cleansing the skin. The emulsion de-emulsifies upon contact with the skin.

The following is a non-limiting example of a fine fragrance system according to the present invention.

TABLE VI

| | Weight % | | | |
|---|---|---|---|---|
| Ingredients | 25 | 26 | 27 | 28 |
| Pro-fragrance¹ | 0.4 | 0.1 | — | — |
| Pro-fragrance² | — | 0.4 | — | — |
| Pro-fragrance³ | — | 0.5 | — | — |
| Photo-labile pro-fragrance⁴ | 0.03 | 0.5 | 1 | 5 |
| δ-Damascone | — | 0.01 | trace | — |
| Geraniol | — | 0.03 | trace | — |
| 9-Decen-1-ol | — | 0.03 | — | — |
| Coumarin | — | 0.005 | — | — |

TABLE VI-continued

| | Weight % | | | |
|---|---|---|---|---|
| Ingredients | 25 | 26 | 27 | 28 |
| Other free fragrance raw materials⁵ | 14 | 17 | 15 | 12 |
| Carrier⁶ | balance | balance | balance | balance |

¹·Pro-fragrance which releases δ-damascone, for example

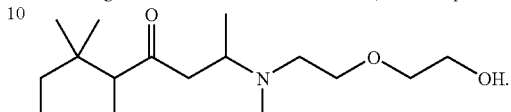

²·Pro-fragrance which releases geraniol; for example

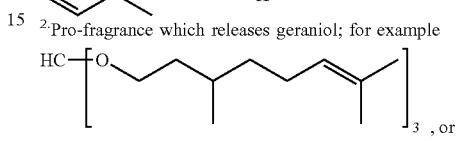

³·Pro-fragrance which releases 9-decen-1-ol; for example

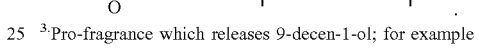

⁴·According to Example 1.
⁵·Conventional fragrance accord.
⁶·Ethanol:water mixture (between 100:0 and 50:50).

What is claimed is:

1. A compound having the formula:

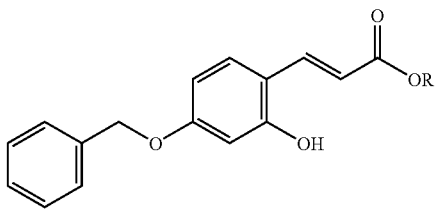

wherein OR derives from a fragrance raw material alcohol selected from the group consisting of 4-(1-methylethyl)cyclohexanemethanol, 2,4-dimethyl-3-cyclohexen-1-yl-methanol, 2,4-dimethylcyclohex-1-ylmethanol, 2,4,6-trimethyl-3-cyclohexen-1-ylmethanol, 2-phenylethanol, 1-(4-isopropylcyclohexyl)ethanol, 2-(o-methylphenyl)ethanol, 2-(m-methylphenyl)ethanol, 2-(p-methylphenyl)ethanol, 2,2-dimethyl-3-(3-methylphenyl)propan-1-ol, 3-phenyl-2-propen-1-ol, 2-methyl-4-(2,2,3-trimethyl-3-cyclopenten-1-yl)-2-buten-1-ol, 3-methyl-5-phenylpentan-1-ol, 3-methyl-5-(2,2,3-trimethyl-3-cyclopenten-1-yl)-4-penten-2-ol, 2-methyl-4-phenylpentan-1-ol, cis-3-hexen-1-ol, 3,7-dimethyl-6-octen-1-ol, 3,7-dimethyl-2,6-octadien-1-ol, 7-methoxy-3,7-dimethyloctan-2-ol, 6,8-dimethylnonan-2-ol, cis-6-nonen-1-ol, 2,6-nonadien-1-ol, 4-methyl-3-decen-5-ol, benzyl alcohol, 2-methoxy-4-(1-propenyl)phenol, 2-meth oxy-4-(2-propenyl)phenol, 4-hydroxy-3-methoxybenzaldehyde, and mixtures thereof.

2. A composition, said composition comprising:
 a) from about 0.001% to about 50% by weight, of a photo-labile pro-fragrance according to claim 1;
 b) optionally from about 0.001% to about 50% by weight, of one or more fragrance raw materials; and
 c) the balance laundry, personal care or laundry softener carriers and adjunct ingredients.

* * * * *